United States Patent [19]
Greenhut et al.

[11] Patent Number: 5,817,134
[45] Date of Patent: Oct. 6, 1998

[54] APPARATUS AND METHOD FOR DETECTING ATRIAL FIBRILLATION BY MORPHOLOGICAL ANALYSIS

[76] Inventors: Saul E. Greenhut, 3586 S. Waco St., Aurora, Colo. 80013; Dean J. MacCarter, 5884 S. Macon, Englewood, Colo. 80011

[21] Appl. No.: 805,769

[22] Filed: Feb. 25, 1997

[51] Int. Cl.⁶ .................................................. A61N 1/362
[52] U.S. Cl. ............................................. 607/14; 600/518
[58] Field of Search ................................. 600/515, 516, 600/517, 518; 607/14, 4, 5

[56] References Cited

U.S. PATENT DOCUMENTS

| | | |
|---|---|---|
| 4,552,154 | 11/1985 | Hartlaub . |
| 5,000,189 | 3/1991 | Throne et al. . |
| 5,086,772 | 2/1992 | Larnard et al. ............................. 607/4 |
| 5,193,550 | 3/1993 | Duffin ..................................... 600/515 |
| 5,215,098 | 6/1993 | Steinhaus et al. ....................... 600/515 |
| 5,273,049 | 12/1993 | Steinhaus et al. . |
| 5,464,433 | 11/1995 | White et al. . |
| 5,480,413 | 1/1996 | Greenhut et al. . |

OTHER PUBLICATIONS

A Technique for Measurement of the Extent of Spatial Organization of Atrial Activation During Atrial Fibrillation in the Intact Human Heart, Gregory W. Bottern and Joseph M. Smith, Member IEEE, IEEE Transactions on Biomedical Engineering, vol. 42, No. 6, Jun. 1995.

Quantitative Assessment of the Spatial Organization of Atrial Fibrillation in the Intact Human Heart, Gregory W. Botteron, MD; Joseph M. Smith, MD, PhD, vol. 93, No. 3, Feb. 1,1996.

*Primary Examiner*—William E. Kamm
*Assistant Examiner*—Kennedy J. Schaetzle
*Attorney, Agent, or Firm*—Gottlieb, Rackman & Reisman

[57] ABSTRACT

In an implantable cardiac device, atrial signals, spaced either spatially or temporally, are sensed and stored. The morphology of the signals are compared and an atrial fibrillation indication is generated if the signals are different. The device then either changes its mode of operation or applies appropriate therapy.

19 Claims, 8 Drawing Sheets

APPARATUS AND METHOD FOR DETECTING ATRIAL FIBRILLATION BY MORPHOLOGICAL ANALYSIS

BACKGROUND OF THE INVENTION

A. Field of Invention

The subject invention pertains to cardiac implants such as pacemakers, and more particularly, to an implanted pacemaker having means for detecting atrial fibrillation (AF) by the morphological analysis of spatially or temporally spaced waveforms. In this application, the term "pacemaker" is used generically to cover implantable cardioverter/defibrillator and other implantable arrhythmia detection devices as well.

B. Description of the Invention

The mechanism for atrial fibrillation is not understood completely. It is believed that it consists of multiple re-entrant depolarization circuits within the atrial chamber. These multiple circuits cause an erratic sequence of atrial depolarizations. Atrial fibrillation is characterized by P waves having amplitudes which are generally smaller than during sinus rhythm and tend to vary from one depolarization to the next. Moreover, the depolarization waveform shape during atrial fibrillation tends to be different than during sinus rhythm, tends to vary from one depolarization to the next, and tends to vary from one electrode location to the next.

Atrial fibrillation is undesirable because it may lead to increased ventricular rate and instability which is uncomfortable for the patient or to formation of thrombi causing a stroke and death. In addition, the atrial rate is used in some pacemakers as a criteria for switching from a dual chamber trigger mode to a single or dual chamber non-trigger mode alleviating pacemaker caused symptoms. In addition, defibrillators may use the atrial rate to distinguish between types of tachycardia which require different types therapy (i.e., antitachycardia pacing, cardioversion or defibrillation). Some cardiac devices are provided with atrial defibrillators to trigger defibrillation therapy, or to trigger drug therapy, for example by activating an implanted drug infusion pump. In these devices, during atrial fibrillation, normal atrial rate detection methods may be ineffective because of the low atrial fibrillation signal amplitude and variability, as discussed above.

Several schemes have been used in the past to detect atrial fibrillation, however none of them have proven to be satisfactory. One such method typically used in pacemakers includes filtering followed by amplitude threshold detection. The resulting atrial rate is then used to classify the rhythm as normal or pathological. However, the frequency response of normal atrial electrograms and those due to AF are typically different, causing electrogram sensing difficulties with this method. Another such scheme involved sensing an atrial electrogram and measuring a variance of the amplitude for a plurality of atrial events. The patient's condition is then identified as one of several categories. However, this method is not as accurate as the method disclosed here since this amplitude 1) may vary during sinus rhythm, 2) may not vary during AF or during other atrial tachyarrhythmia, and 3) may not distinguish true depolarization from noise. Hence, amplitude variance by itself is not necessarily indicative of atrial fibrillation. Details of this method are found in commonly assigned co-pending application Ser. No. 730,748 filed Oct. 15, 1996, now U.S. Pat. No. 5,720,295, entitled PACEMAKER WITH IMPROVED DETECTION OF ATRIAL FIBRILLATION.

Another proposed scheme involved spectral analysis of the sensed atrial events. However, this type of analysis requires a very high computational level which is beyond the capabilities of present implantable cardiac devices.

Another proposed scheme involved analyzing atrial events at low frequencies, i.e., using band pass filters at lower bands than presently in use. However, this scheme is undesirable because it emphasizes the low frequency components of the ventricular depolarization and repolarization signal which may then be incorrectly sensed by the atrial channel.

A natural approach would be to increase the sensitivity of the atrial channel by increasing the amplification gain. However, increasing this gain also renders the device prone to noise or far-field ventricular events.

A further scheme involves using an activation sequence and timing of atrial and ventricular depolarization events. However, this method has the same atrial signal detection deficiencies as the above methods.

OBJECTIVES AND SUMMARY OF THE INVENTION

In view of the above, it is an objective of the present invention to provide an implantable cardiac device with an improved atrial fibrillation detector.

A further objective is to provide an atrial fibrillation detector which may be implemented using present day pacemaker technology.

Yet a further objective is to provide a dual chamber pacemaker, with a fast and accurate means of detecting atrial fibrillation.

Other objectives and advantages of the invention shall become apparent from the following description of the invention. Briefly, a cardiac device constructed in accordance with this invention includes a pace and sense circuit providing interfacing with the outside world and a digital microprocessor receiving signals from the pace and sense circuit and providing, in response, control signals for cardiac pacing. A detector detects atrial fibrillation and transmits a corresponding signal to the microprocessor which then applies appropriate therapy, if necessary. In some instances, other steps may be taken to classify the arrhythmia. The detector may be implemented as an integral part of the microprocessor.

More particularly, in order to detect atrial fibrillation, two waves sensed in the atrium indicative of intrinsic atrial events are compared, morphologically for example, by performing a correlation thereon. The two waves are separated either temporally or spatially. A close correlation between successive wave measurements indicates a sinus rhythm while a large variation between successive wave measurements is indicative of atrial fibrillation.

DETAILED DESCRIPTION OF THE INVENTION

Figure 1:
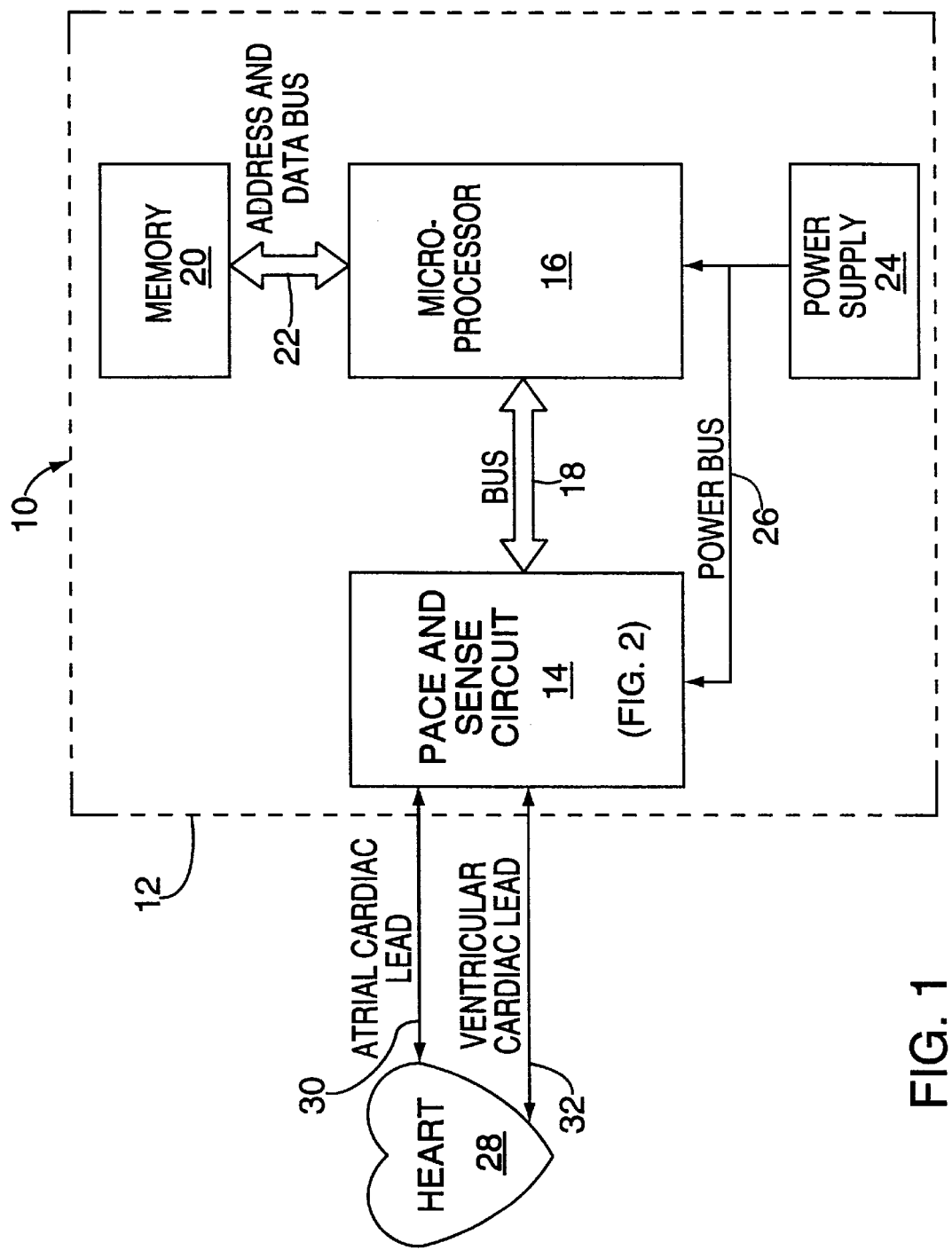
FIG. 1 shows a generalized block diagram of a pacemaker constructed in accordance with this invention.

For the sake of simplicity, an implantable pacemaker operating in a dual chamber mode (for example, DDDR or DDD) shall now be described, it being understood that the invention is easily adaptable by one skilled in the art to other implantable cardiac devices as well. Referring now to FIG. 1, a pacemaker 10 constructed in accordance with this invention includes an implantable housing 12. The housing holds a pace and sense circuit 14, described in more detail in FIG. 2, and a microprocessor 16. The pace and sense circuit 14 and the microprocessor 16 are interconnected by a bus 18 for exchanging data, as well as communication and control signals. The pacemaker 10 further includes a memory 20 connected to the microprocessor 16 by a data and address bus 22, and a power supply 24 providing power to the various components of pacemaker 10 via power bus 26. Communication with an external programmer is provided by a telemetry circuit which has been omitted in the figures for the sake of clarity.

Once implanted, the pacemaker 10 is connected to a patient's heart 28 by two leads 30, 32. Preferably, these leads 30, 32 are bi-polar leads with lead 30 being connected to the atrial chamber of the heart, and lead 32 being connected to the ventricular chamber. Therefore, leads 30 and 32 are known as the atrial cardiac lead and the ventricular cardiac lead, respectively. It should be understood that the arrangement of the pacemaker 10 and leads 30 and 32 do not form a part of this invention. Other arrangements may be used as well, using other types of leads including tri-polar leads, a single-pass quadripolar lead, unipolar leads, multiple leads in atrial and/or ventricular chambers, and so on.

Figure 2:
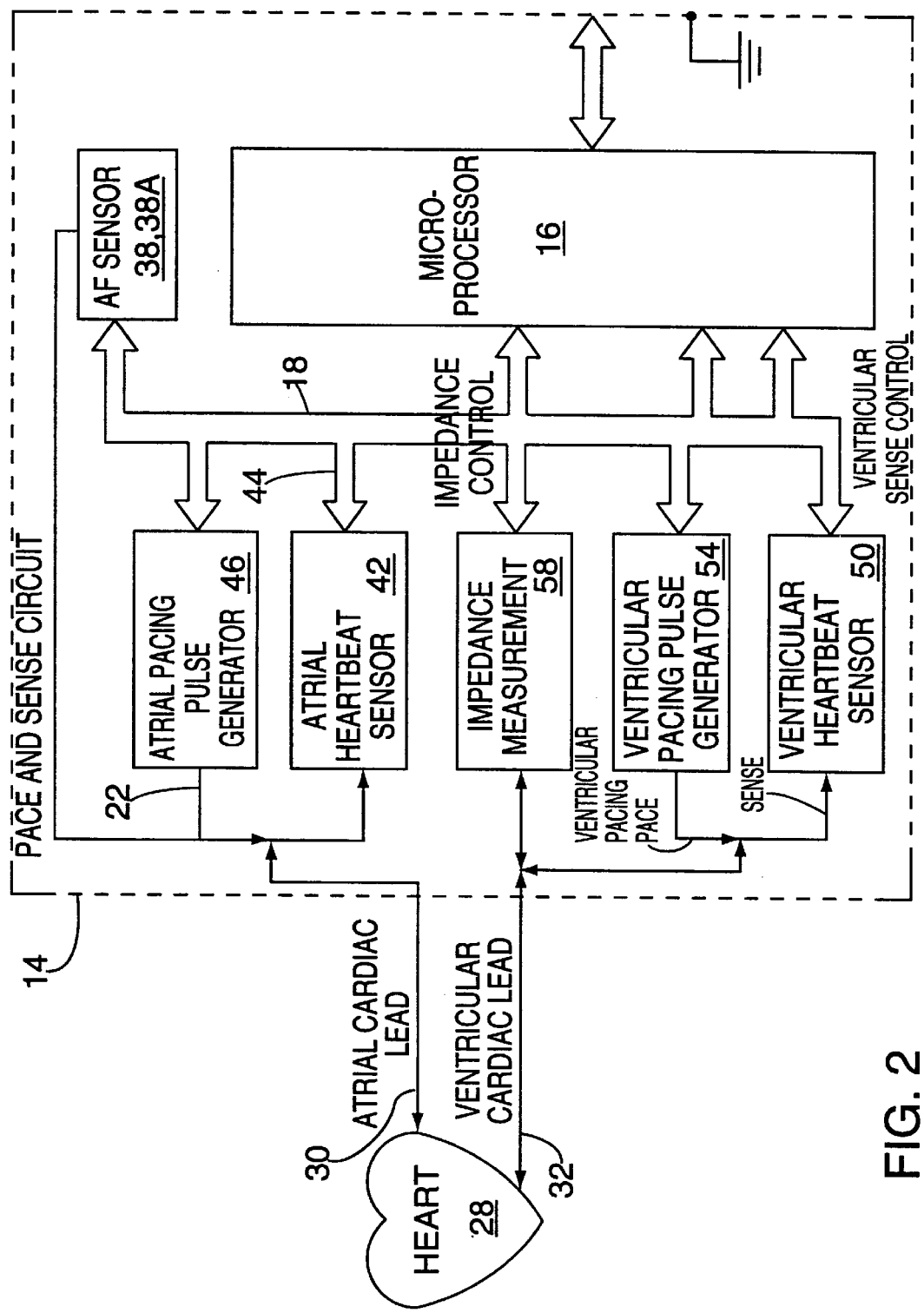
FIG. 2 shows a more detailed block diagram of the pacemaker of FIG. 1.

Referring now to FIG. 2, the pace and sense control circuit 14 includes various sensing and control circuits for sensing the status of the chambers of heart 28 and to provide appropriate pacing signals thereto. The bus 18 provides interfacing between the various components and microprocessor 16.

More specifically, signals from the atrium are sensed through lead 30 by the atrial heartbeat sensor 42. Atrial pacing pulses are generated for lead 30 by atrial pacing pulse generator 46. Similarly, the ventricular chamber is sensed through lead 32 by ventricular heartbeat sensor 50. Pacing pulses for the ventricular chamber are generated by the ventricular pacing pulse generator 54.

In addition, the transthoracic impedance is measured between one of the cardiac leads, such as lead 32, and the pacemaker housing by impedance measurement circuit 58 and used to generate a metabolic indicated rate parameter used by the microprocessor for generating pacing pulses.

Except as noted below, the operation of the pacemaker 10 illustrated in FIGS. 1 and 2 is described in commonly assigned U.S. Pat. No. 5,480,413 by T. A. Nappholz, entitled FORCED ATRIO-VENTRICULAR SYNCHRONY DUAL CHAMBER PACEMAKER, and incorporated herein by reference.

Importantly, the pacemaker 10 further includes an atrial fibrillation sensor 38 coupled to the bus 18. The sensor 38 may be implemented by discrete logic elements, in which case it may be incorporated into the atrial heartbeat sensor 42, it may be implemented by software within the microprocessor 16, or by a combination of these two schemes. The AF sensor may also detect atrial events using more sensitive detection methods (i.e., a different band-pass filter) or may rely on the atrial heart beat sensor 42.

Figure 3:
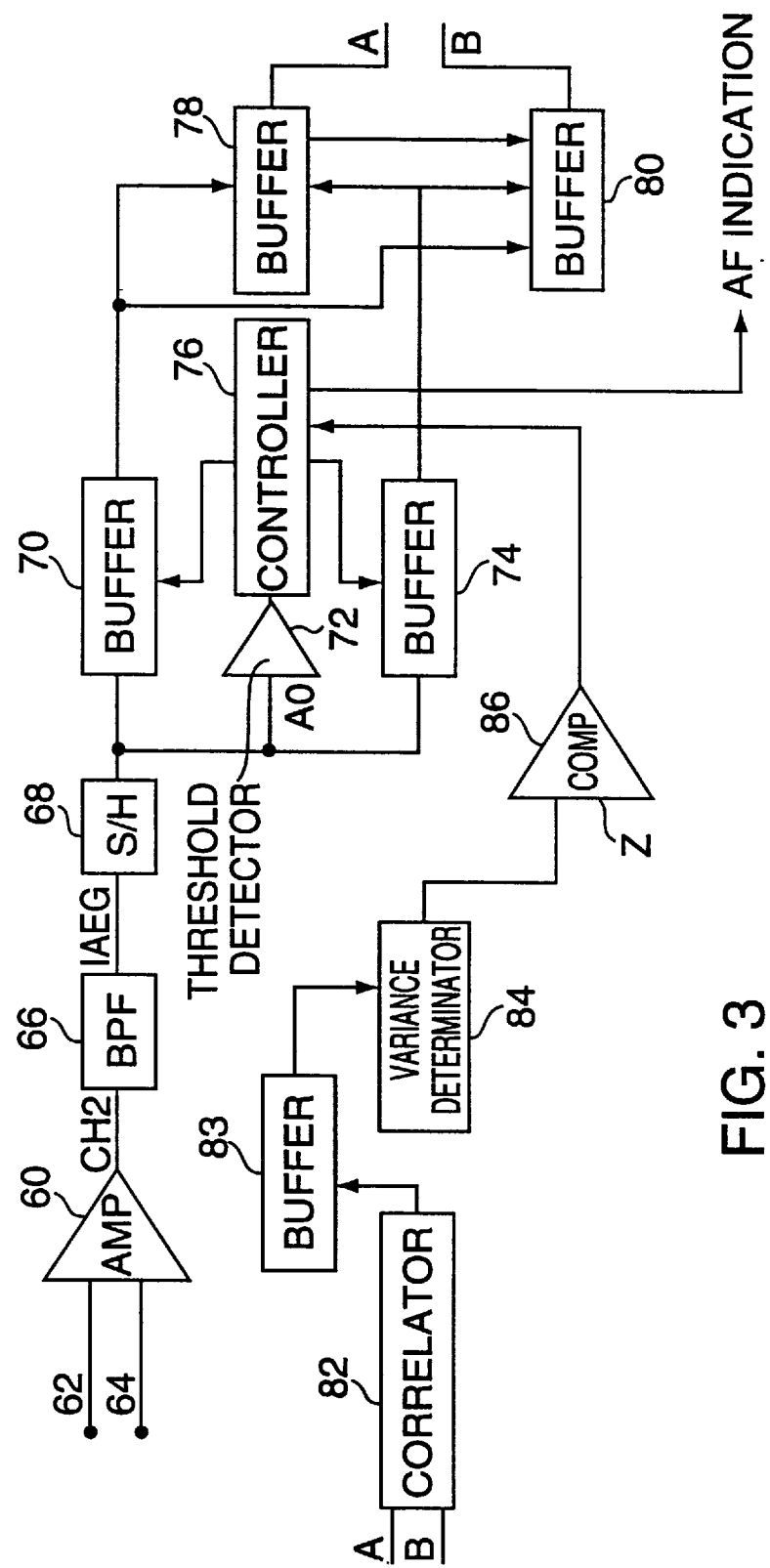
FIG. 3 shows a block diagram for a first embodiment of the atrial fibrillation sensor of FIG. 2.

Referring now to FIG. 3, in one embodiment, the atrial fibrillation sensor 38 includes an amplifier 60 used for sensing atrial activity. For this purpose the amplifier has two inputs 62 and 64. These inputs are connected to either the two atrial electrodes of lead 30 in a bipolar mode, or to one of said atrial electrodes and the pacemaker case in a unipolar mode. The output of amplifier 60 is fed to a band pass filter (BPF) 66. Band pass filter 66 is used to generate an intra-atrial electrogram (IAEG) signal or waveform. This signal is sampled by a sample-and-hold (S/H) circuit 68. The samples generated by circuit 68 are fed simultaneously to a circulating buffer 70, a threshold detector 72 and a second buffer 74. The operation of the circuit 38 is controlled by a controller 76 as described below. The circuit 38 further includes two buffers 78, 80 used to store two complete IAEG signals, a correlator 82 to correlate the two IAEG signals, a circulating buffer 83, a variance determinator 84, and a comparator 86.

Figure 4:
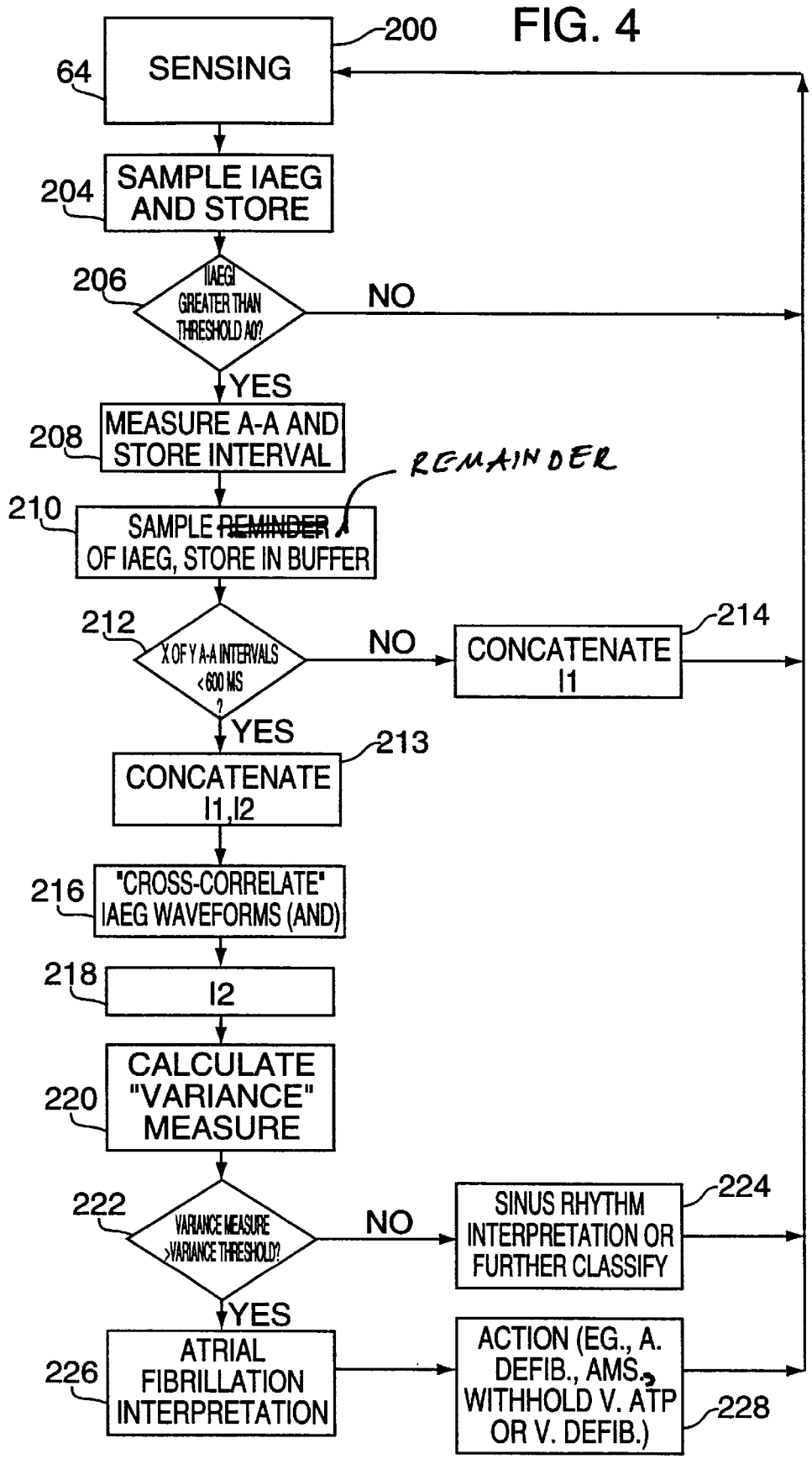
FIG. 4 shows a generalized flow chart for the sensor of FIG. 3.
Figure 5:
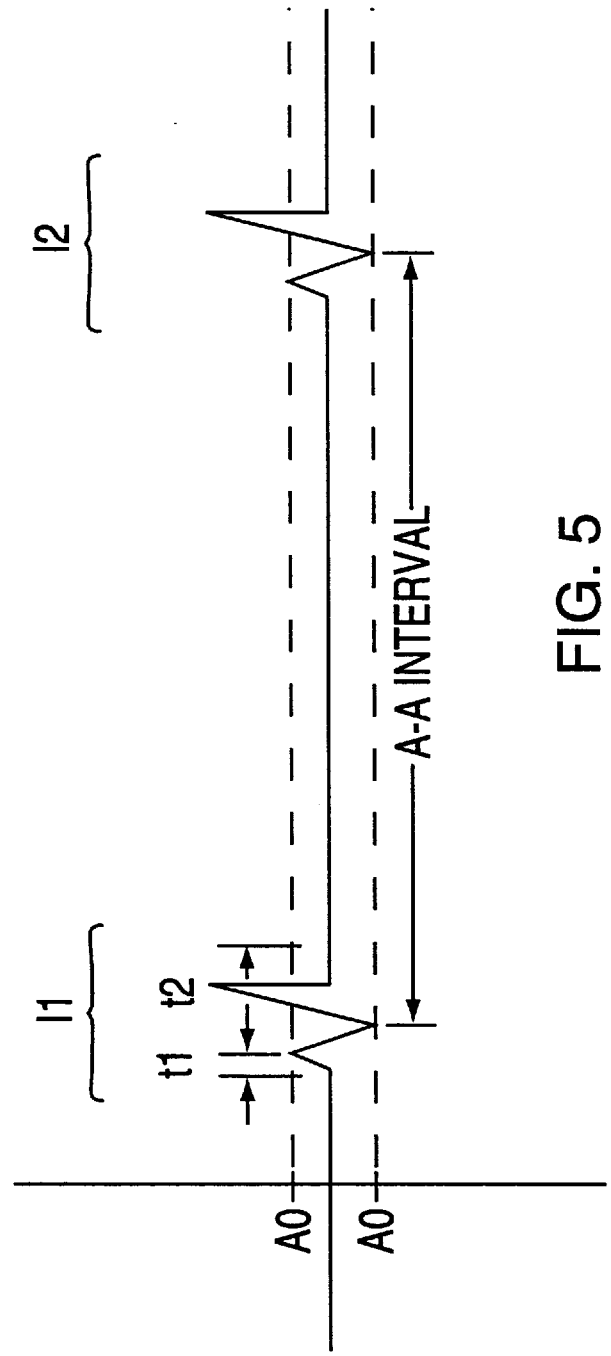
FIG. 5 shows with two temporally spaced IAEG waveforms used for atrial fibrillation detection for the embodiment of FIGS. 3 and 4.
Figure 6:
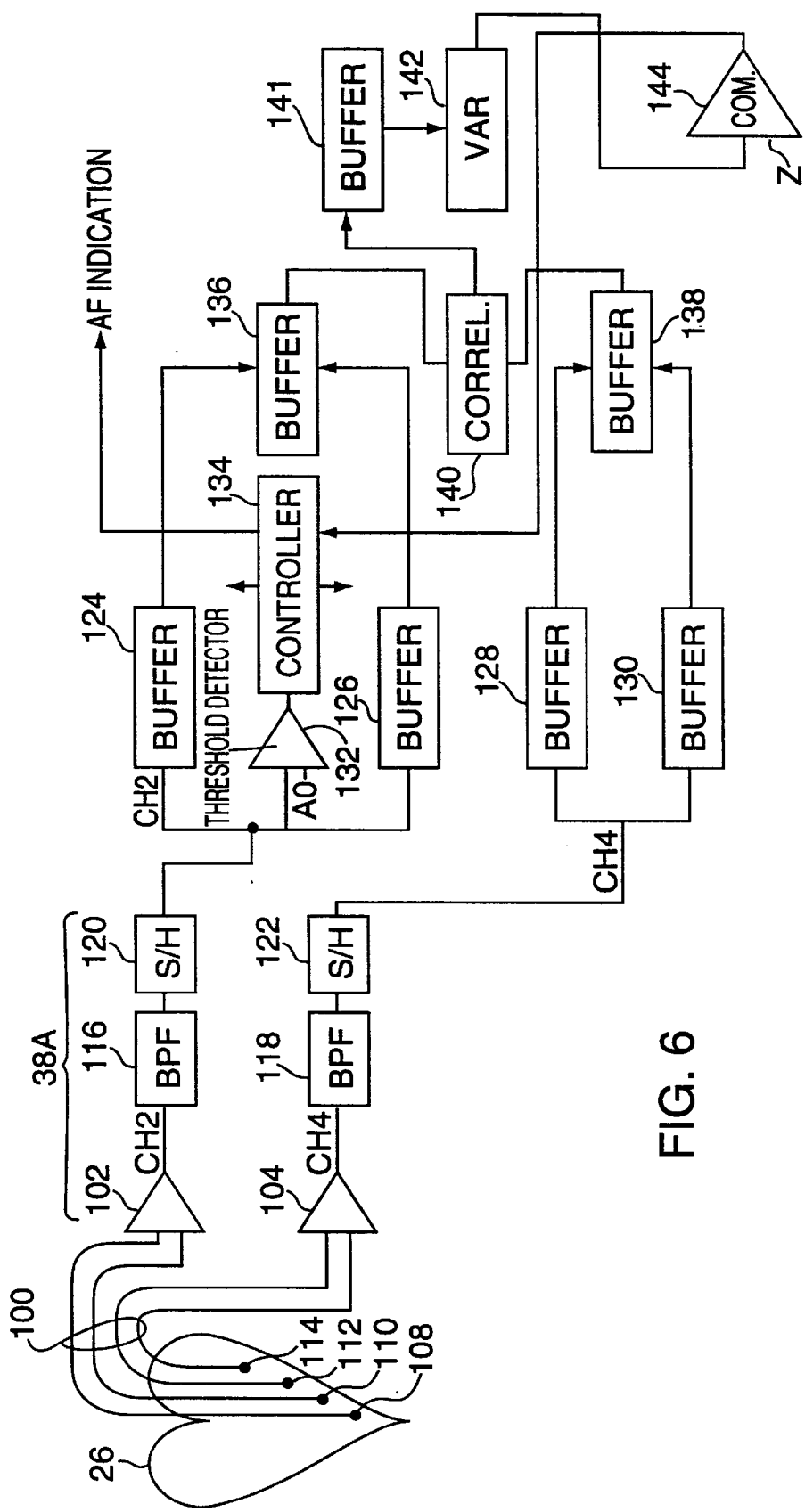
FIG. 6 shows a block diagram of a second embodiment for the atrial fibrillation sensor.

The operation of the sensor 38 is shown in flow chart of FIG. 4. In step 200 the filter 66 filters the signal received at its inputs 62, 64. The signal received from amplifier 60, and filtered by filter 66 is sampled by circuit 68 at preset intervals and stored in buffer 70 in step 204. In step 206 each sample from circuit 68 is also compared to a preset threshold level A0 by threshold detector 72. A typical IAEG signal I1 is shown in FIG. 5. If the threshold detector 72 is set to detect signals having an absolute magnitude exceeding a threshold A0, there will be a period of time t1 before the signal I1 reaches this level A0. Sampled data collected during this time period t1 is collected in buffer 70. When the signal I1 is finally detected ("YES" in step 206), a corresponding signal is sent to controller 76. In step 208 the A—A interval is measured between a previous IAEG signal (not shown) and signal I1. Thereafter, the rest of signal I1 during period t2 is stored in buffer 74 (step 210).

In step 212 a test is performed to monitor the A—A interval. For example, in this step, the determination is made as to whether for the last Y atrial events, X of Y times the interval A—A was smaller than, for example, 600 msec, i.e., the atrial rate exceeded 100 beats per minute. Y could be, for example, 10 and X could be 8. By using a relatively low rate threshold, intermittent atrial sensing does not cause the algorithm to misinterpret AF. If the test of step 212 is not met, the atrial chamber is depolarizing at a relatively slow rate, and a normal sinus rhythm is assumed. In step 214 two sets of samples or portions obtained during t1 and t2 from memories 70 and 74 are transferred under the command of controller 76 and concatenated into buffer 80. Thus, memory 80 contains, in a sampled form, a reproduction of signal I1. The controller now returns to a standby mode and waits for a next atrial event, step 200.

Assume now that after an interval A—A a second signal I2 is detected in a manner similar to I1 and this time the test of step 212 succeeds. Now, the contents of buffers 70 and 74 are summed or concatenated into buffer 78. (Step 213). So, at this point, buffer 78 has a representation of signal I2 and buffer 80 has a representation of signal I1. In step 216 correlator 82 retrieves the contents of the buffers 78, 80, performs a cross correlation and stores the results in circular buffer 83. In step 218 the contents of buffer 78, i.e., signal I2 is stored in buffer 80 thereby replacing signal I1.

In step 220 the variance determinator 84 generates a variance over the correlations of the previous Y depolarizations stored in buffer 83. In step 222 this variance is compared to a threshold Z by comparator 86 and the results are provided to controller 76. If this variance is smaller than the threshold Z, then in step 224 the controller 76 reports to the microprocessor that AF was not found. Next the microprocessor either proceeds with normal pacing functions assuming a normal sinus rhythm or performs other rhythm classification schemes.

If the variance is greater than threshold Z, then in step 226 the controller reports to the microprocessor 16 that atrial fibrillation has been identified. In step 228, then the microprocessor can apply various therapeutic procedures, such as atrial defibrillation, automatic mode switching (AMS), drug infusion, and so on, or it may withhold therapy it might otherwise have delivered including ventricular antitachycardia pacing or ventricular defibrillation.

In steps 216 and 220 correlation (or cross-correlation) and variance are used as a means of determining whether the signals I1 and I2 are morphologically comparable or not. The term 'correlation' is not used in the strictly mathematical sense but is meant to cover generically any kind of morphological comparison between the two waveshapes. Correlation means include correlation waveform analysis, normalized area of difference analysis, signature analysis (see U.S. Pat. No. 5,273,049), derivative area (see U.S. Pat. No. 5,000,189), all incorporated by reference, and so on. Correlation may also refer to determining the similarity between individual waveform features which may include, for example, waveform amplitude, width, polarity, and so on. Similarly, the term 'variance' is used herein not necessarily in the statistical sense but to any indicia of a variation in the signal morphology. Methods of determining this variance are disclosed in U.S. Pat. No. 5,480,413 incorporated herein by reference.

In any case, the sensor of FIG. 3 detects atrial fibrillation by comparing the morphology of two signals I1 and I2 which are sensed using the same electrode configuration but are separated temporally. Preferably, the signals I1 and I2 are consecutive. However, they may also be separated by several A—A intervals, in which case several intermediate atrial intrinsic events are skipped.

When determining if the variance is high, (step 222) instead of a preset threshold, an average value, for example derived from several (i.e., 8) atrial events during normal sinus rhythm may be used instead.

In the embodiment of FIGS. 6–9, atrial signals are used which are spatially separated. That is, two waveforms (IAEGs) from different sections of the atrium are sensed simultaneously and correlated to identify atrial fibrillation. More specifically, sensor 38A shown in FIG. 6 includes two amplifiers 102, 104 having inputs connected to a quatripole lead 100. The distal end 106 of lead 100 is threaded into the heart 26 and is provided with atrial electrodes 108, 110, 112, 114. The technique described herein may also be used with a tripolar lead wherein one of the electrodes is used as a common return for the other two, or two bipolar leads or leads of other configurations which can supply two spatially separated signals to amplifiers 102, 104. Amplifier 102 has its inputs connected to atrial electrodes 112, 114, while amplifier 104 has inputs connected to atrial electrodes 108, 110, as shown. In addition, the wires for all these electrodes are connected to the sensing and pacing circuitry described in FIG. 2, however these latter connections are omitted in FIG. 6 for the sake of simplicity.

Figure 8:
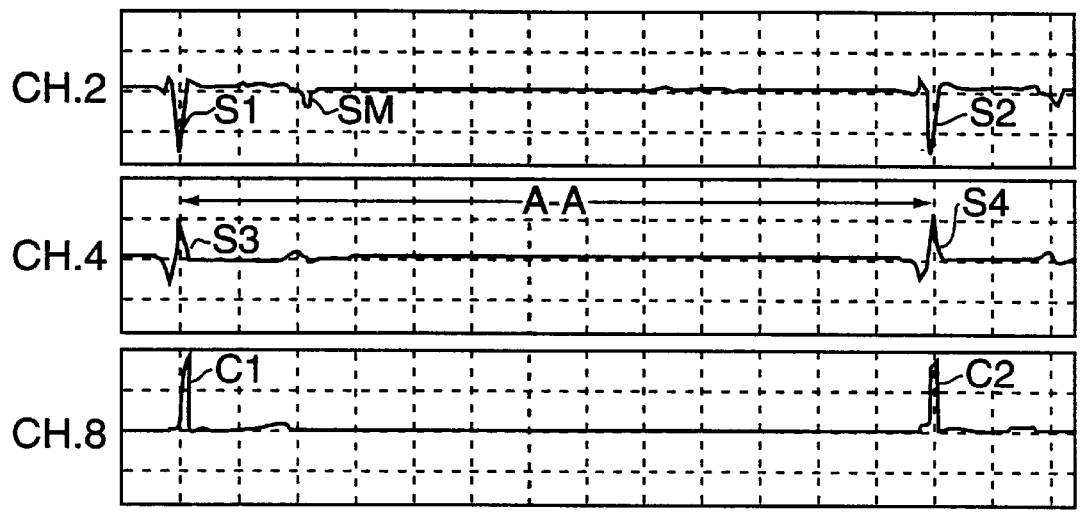
FIG. 8 shows two simultaneous, spatially spaced normal sinus rhythm IAEG wave forms for the embodiment of FIGS. 6 and 7.
Figure 9:
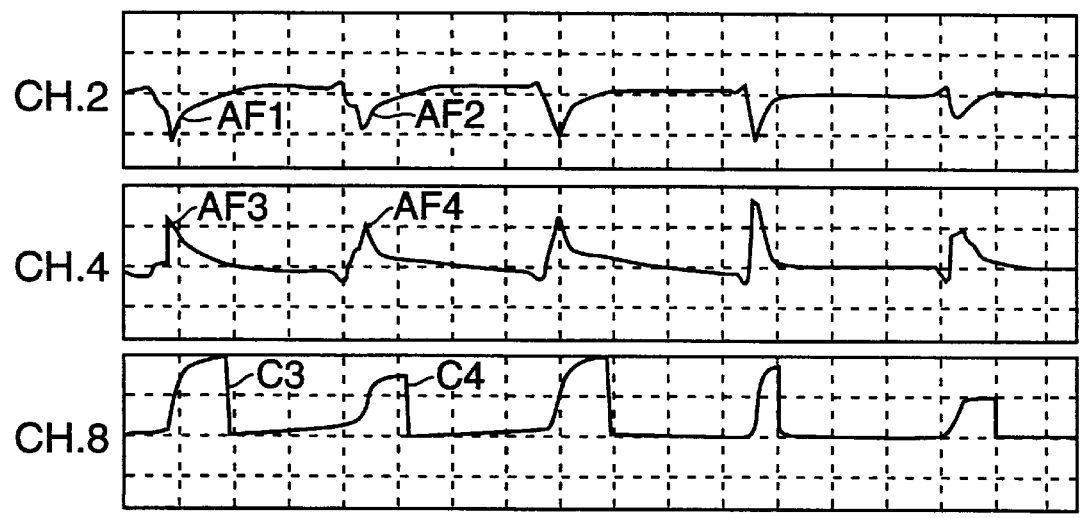
FIG. 9 shows two simultaneous, spatially spaced IAEG wave forms indicative of atrial fibrillation for the embodiment of FIGS. 6 and 7.

The output signals from the amplifiers are fed respectively to band pass filters 116, 118 and from there to respective sample-and-hold circuits 120, 122. FIGS. 8 and 9 show typical waveforms output by amplifiers 102 and 104 after filtering. More specifically, the filtered output of amplifier 102 is shown in both Figures as channel 2 and the filtered output of amplifier 104 is indicated by channel 4. The outputs of the S/H circuits are fed respectively to two buffers 124, 126, 128, 130, each, as shown. In addition, the output of one of the S/H circuits, for example, S/H circuit 120, is also fed to a threshold detector 132. The operation of the atrial fibrillation sensor 38A is controlled by controller 134, as described below. The buffers 124, 126 and 128, 130, feed their contents to buffers 136, 138, respectively. The contents of these buffers are selectively correlated under the direction of controller 134 by a correlator 140. Cross correlation may be performed by using a normalized area of the differences between the signal or other known means, such as those discussed for step 216 above. A plurality of past correlations is stored in circulating buffer 141. The variance of these correlations is determined by a variance determinator 142. Determinator 142 may use the same techniques as the one described above. This variance is compared to a preset value Z by comparator 144 to determine if atrial fibrillation is indicated. This decision is then fed to controller 134 for further action, if required.

Figure 7:
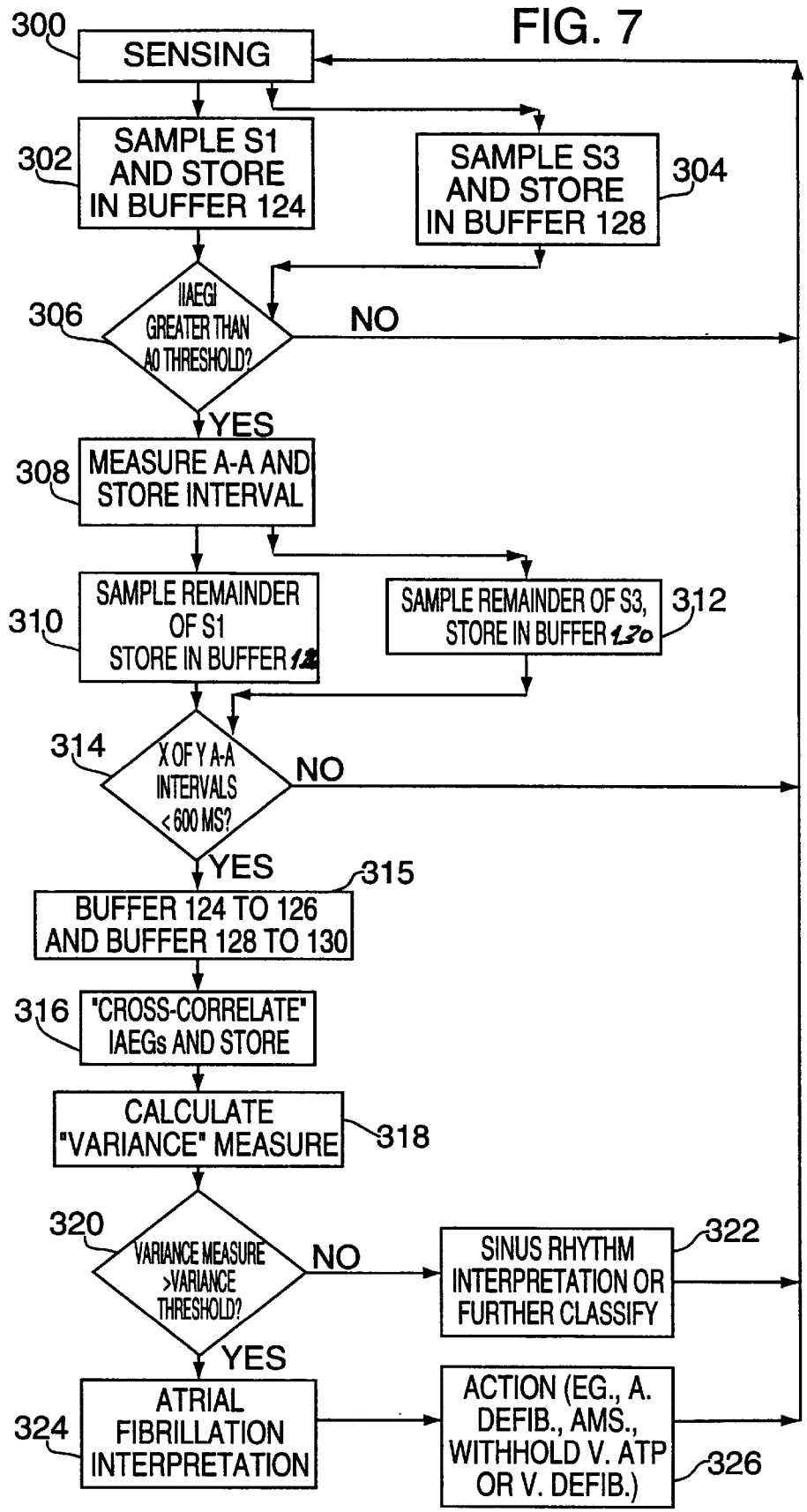
FIG. 7 shows a flow chart for the embodiment of FIG. 6.

The operation of the sensor 38A is now explained in conjunction with the flow chart of FIG. 7 and the waveforms of FIGS. 8 and 9. FIG. 8 shows two consecutive IAEG signals S1, S2 obtained by amplifier 102, during an interval A—A, as indicated on FIG. 8 on channel 2. A third signal SM has an amplitude which is smaller than the threshold A0 of comparator 132 and therefore, it is omitted. Simultaneously, two other signals S3 and S4 are obtained from amplifier 104, as indicated on FIG. 8 by channel 4. The correlation between signals S1 and S3 is shown in FIG. 8, as C1 on channel 8. Similarly, the correlation between simultaneous signal S2 and S4 is shown by signal C2. C1 and C2 are indicative of a high correlation, low variance between the signals on channels 2 and 4 and are interpreted as normal sinus rhythm.

On FIG. 9, signals AF1, AF2, on channel 2 and signals AF3, AF4 on channel 4 are typical of atrial fibrillation. The correlation between signals AF1 and AF3 is indicated by signal C3 while the correlation between AF2 and AF4 is shown by C4. Comparing C3 and C4 shows an increased variance characteristic of atrial fibrillation.

In step 300 the waveforms sensed from the electrodes 108–114 are amplified and filtered. In steps 302, 304 the signals are sampled and fed into respective circulating buffers 124, 128. As this process is going on, the signals from amplifier 102 are fed to threshold detector 132. When this detector (step 306) detects a signal exceeding a preselected threshold level A0, it generates a corresponding signal to controller 134. In step 308 the controller measures the interval A—A between the current atrial event and the previous atrial event. In steps 310, 312, the controller disables circulating buffers 124, 128 and feeds the remainder of the IAEG signals to buffers 126, 130.

In step 314 an X out of Y test is performed on the A—A interval. This step is identical to step 212 of FIG. 4. If the test fails normal sinus rhythm is assumed. If step 314 determines that the A—A interval meets the test, then morphological testing is performed on the IAEG signals as follows. In step 315 the samples from buffers 124 and 126 are concatenated into buffer 136 so that they represent a continuous IAEG. Similarly, the samples from buffers 128, 130 are concatenated into buffer 138. The resulting signals are cross correlated by correlator 140 in step 316 and stored in buffer 141. Typical correlation relative values are shown in FIGS. 8 and 9 identified as channel 8.

In step 318 the variance of this cross-correlation is determined by variance determinator 142. In step 320 this variance is compared by comparator 144 to a preset threshold level. A low variance is indicative of a normal sinus rhythm to the controller 134. The controller sends this information to the microprocessor 16 which then operates the pacemaker accordingly. If other indicia show a cardiac irregularity, other classifying means are used by the microprocessor to analyze this problem (step 322).

If the variance is high, the controller 134 receives an indication of atrial fibrillation (Step 324). This information is passed on to the microprocessor for generating an appropriate action, i.e., atrial defibrillation, Automatic Mode Switching, drug therapy or withhold therapy, such as ventricular defibrillation or ventricular antitachycardia pacing which would have otherwise been applied. (Step 326).

The windows during which various initial buffers collect sampled data are preset. For example, the buffer 70, 124, 128 may be set to collect data for 20 msec, while buffer 74, 126, 130 may collect data for 40 msec.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. In an implantable cardiac device, an atrial fibrillation detector comprising:
    an atrial sensor for sensing a first and a second atrial signal, said atrial signals being spaced in one of a spacial and temporal domain;
    a first and a second storage for storing said first and second atrial signals, respectively;
    a morphological comparator coupled to said storages for comparing said first and second atrial signals; and
    an atrial fibrillation indicator for generating a signal indicative of atrial fibrillation based on said morphological comparator.

2. The detector of claim 1 further comprising a pair of electrodes and wherein said first and second atrial signals are sensed sequentially from said pair of electrodes.

3. The detector of claim 2 wherein said pair of electrodes includes two unipolar or bipolar leads.

4. The detector of claim 2 wherein said pair of electrodes includes an electrode for disposal in the heart and a casing for said device.

5. The detector of claim 1 further comprising includes a first electrode pair and a second electrode pair, and wherein said first signal is obtained from said first electrode pair and said second signal is obtained from said second electrode pair.

6. The detector of claim 5 wherein said first and second storages are constructed and arranged to store said signal simultaneously.

7. A dual chamber pacemaker comprising:
    an atrial sensor for sensing intrinsic atrial activity;
    an atrial pacer for generating atrial pulses in response to atrial pace commands;
    a ventricular sensor for sensing ventricular activity;
    a ventricular pacer for generating ventricular pulses in response to ventricular pace commands;
    an atrial fibrillation detector for generating an atrial fibrillation detection signal; and
    a controller receiving signals indicative of said atrial and ventricular activity and said atrial fibrillation detection signal, said controller generating said command signals;
    said atrial fibrillation detector including:
        a sensor for sensing two spaced atrial signals; and
        a morphological analyzer comparing the morphology of said atrial signals, said analyzer generating said atrial fibrillation detection signal if the morphology indicates a difference in said signals.

8. The pacemaker of claim 7 wherein said atrial signals are spatially spaced.

9. The pacemaker of claim 7 wherein said atrial signals are temporally spaced.

10. The pacemaker of claim 7 wherein said analyzer includes a correlator for correlating said signals.

11. The pacemaker of claim 10 wherein said analyzer further includes a variance circuit for generating a variance based on said correlation.

12. The pacemaker of claim 7 wherein said detector includes a duration sensor for sensing an A—A time interval between two atrial signals, wherein said atrial fibrillation detection signal is generated if said interval indicates a high atrial rate.

13. The pacemaker of claim 7 wherein said controller includes an Automatic Mode Switch means responsive to said atrial fibrillation signal for generating pacing commands independent of the atrial activity.

14. In an implantable cardiac device having means for sensing atrial activity and means for applying cardiac therapy in response, a method of detecting atrial fibrillation comprising the steps of:
    sensing two spaced atrial signals;
    comparing morphologically said atrial signals; and
    generating an atrial fibrillation indication signal if said signals are different.

15. The method of claim 14 wherein said atrial signals are sensed sequentially.

16. The method of claim 14 wherein said device includes a first pair of electrodes and a second pair of electrodes and wherein said signals are sensed simultaneously, said first signal being sensed from said first pair and said signal being sensed from said second pair.

17. The method of claim 14 wherein said step of comparing includes correlating said signals.

18. The method of claim 17 wherein said step of comparing includes obtaining a variance of said signals based on said correlation.

19. The method of claim 18 further comprising comparing said variance to a threshold.

* * * * *